(12) United States Patent
Quatieri et al.

(10) Patent No.: US 10,561,361 B2
(45) Date of Patent: Feb. 18, 2020

(54) USING CORRELATION STRUCTURE OF SPEECH DYNAMICS TO DETECT NEUROLOGICAL CHANGES

(71) Applicant: Massachusetts Institute of Technology, Cambridge, MA (US)

(72) Inventors: Thomas F. Quatieri, Newtonville, MA (US); James R. Williamson, Arlington, MA (US); Brian Helfer, Arlington, MA (US); Rachelle Laura Horwitz-Martin, Acton, MA (US); Bea Yu, Lexington, MA (US); Daryush Dinyar Mehta, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 979 days.

(21) Appl. No.: 14/518,490

(22) Filed: Oct. 20, 2014

(65) Prior Publication Data
US 2015/0112232 A1 Apr. 23, 2015

Related U.S. Application Data

(60) Provisional application No. 61/893,247, filed on Oct. 20, 2013.

(51) Int. Cl.
*A61B 5/00* (2006.01)
*A61B 5/16* (2006.01)
*A61B 5/11* (2006.01)

(52) U.S. Cl.
CPC ............ *A61B 5/4803* (2013.01); *A61B 5/165* (2013.01); *A61B 5/7264* (2013.01); *A61B 5/11* (2013.01);
(Continued)

(58) Field of Classification Search
CPC ...... A61B 3/113; A61B 5/4064; A61B 5/4082; A61B 8/0808
(Continued)

(56) References Cited

U.S. PATENT DOCUMENTS 4,543,957 A * 10/1985 Friedman ................. A61B 5/16
600/300
5,790,754 A * 8/1998 Mozer ..................... G10L 15/16
704/232
(Continued)

FOREIGN PATENT DOCUMENTS

WO WO 2015/102733 7/2015

OTHER PUBLICATIONS

Bagby, R.M., et al., "The Hamilton Depression Rating Scale: Has the Gold Standard Become a Lead Weight?", *Am J Psychiatry* 161: 2163-2177 (2004).
(Continued)

*Primary Examiner* — May A Abouelela
(74) *Attorney, Agent, or Firm* — Occhiuti & Rohlicek LLP

(57) ABSTRACT

A method and a system for assessing a condition in a subject. An example of a condition is a Major Depressive Disorder (MDD). The method comprises measuring at least one speech-related variable in a subject; extracting a channel-delay correlation structure of the at least one speech-related variable; and generating an assessment of a condition of the subject, based on the correlation structure of the at least one speech-related variable.

16 Claims, 9 Drawing Sheets
(8 of 9 Drawing Sheet(s) Filed in Color)

(52) U.S. Cl.
CPC ........... *A61B 5/4064* (2013.01); *A61B 5/4082* (2013.01); *A61B 5/4088* (2013.01); *A61B 5/4815* (2013.01); *A61B 5/742* (2013.01)

(58) Field of Classification Search
USPC ................ 600/300, 587, 595; 704/232, 246; 434/169
See application file for complete search history.

(56) References Cited

U.S. PATENT DOCUMENTS

| | | | | |
|---|---|---|---|---|
| 6,063,028 | A * | 5/2000 | Luciano | G06F 19/3437 128/898 |
| 6,622,036 | B1 * | 9/2003 | Suffin | A61B 5/0006 600/300 |
| 6,816,836 | B2 * | 11/2004 | Basu | G06K 9/00228 382/100 |
| 6,820,053 | B1 * | 11/2004 | Ruwisch | G10L 21/0208 381/94.3 |
| 6,839,669 | B1 * | 1/2005 | Gould | G10L 15/22 704/246 |
| 7,451,079 | B2 * | 11/2008 | Oudeyer | G10L 13/033 704/205 |
| 7,822,600 | B2 * | 10/2010 | Kim | G10L 25/90 704/207 |
| 7,827,031 | B2 * | 11/2010 | Albesano | G10L 15/16 700/48 |
| 8,032,209 | B2 * | 10/2011 | He | A61B 5/04008 600/544 |
| 8,038,614 | B2 * | 10/2011 | Gobeyn | A61B 5/411 382/128 |
| 8,069,049 | B2 * | 11/2011 | Nilsson | G10L 21/0364 704/500 |
| 8,204,747 | B2 * | 6/2012 | Kato | G10L 17/26 704/243 |
| 8,892,424 | B2 * | 11/2014 | Harada | G10L 25/63 704/201 |
| 2002/0103429 | A1 * | 8/2002 | deCharms | A61B 5/055 600/410 |
| 2003/0154079 | A1 * | 8/2003 | Ota | G10L 15/22 704/246 |
| 2004/0019484 | A1 | 1/2004 | Kobayashi | |
| 2004/0254791 | A1 * | 12/2004 | Coifman | G10L 15/26 704/246 |
| 2006/0069559 | A1 | 3/2006 | Ariyoshi | |
| 2008/0147391 | A1 * | 6/2008 | Jeong | G10L 15/02 704/232 |
| 2009/0062686 | A1 * | 3/2009 | Hyde | A61B 5/1112 600/558 |
| 2009/0119103 | A1 * | 5/2009 | Gerl | G10L 17/04 704/243 |
| 2009/0149778 | A1 * | 6/2009 | Naujokat | A61B 5/0002 600/595 |
| 2009/0208913 | A1 * | 8/2009 | Xu | A61B 5/7264 434/169 |
| 2011/0004126 | A1 * | 1/2011 | Einav | G06F 19/3481 600/595 |
| 2011/0135069 | A1 * | 6/2011 | Yoshida | H04M 3/42221 379/85 |
| 2012/0323575 | A1 * | 12/2012 | Gibbon | G11B 27/28 704/246 |
| 2013/0090927 | A1 | 4/2013 | Quatieri et al. | |
| 2013/0150684 | A1 * | 6/2013 | Cooner | A61B 5/1101 600/301 |
| 2013/0166291 | A1 | 6/2013 | Lech et al. | |
| 2013/0191127 | A1 * | 7/2013 | Iida | G01S 3/8083 704/246 |
| 2014/0194310 | A1 * | 7/2014 | Geschwind | C12Q 1/6883 506/9 |
| 2014/0257047 | A1 * | 9/2014 | Sillay | A61B 5/11 600/301 |
| 2016/0086600 | A1 * | 3/2016 | Bauer | G10L 15/16 704/202 |

OTHER PUBLICATIONS

Cannizzaro, M., et al.,"Voice Acoustical Measurement of the Severity of Major Depression", *Brain and Cognition* 56(1): 30-35 (2004).

Cohn, J.F., et al., "Detecting Depression from Facial Actions and Vocal Prosody", 3rd *International Conference on Affective Computing and Intelligent Interaction and Workshops* (Sep. 10-12, 2009).

Fava, M. and Kendler, K., "Major Depressive Disorder", *Neuron* 28(2): 335-341 (2000).

Flint, A.J., et al., "Abnormal Speech Articulation, Psychomotor Retardation, and Subcortical Dysfunction in Major Depression", *Journal of Psychiatric Research* 27(3): 309-319 (1993).

France, D.J., et al., "Acoustical Properties of Speech as Indicators of Depression and Suicidal Risk." *IEEE Transactions on Biomedical Engineering* 47(7): 829 (2000).

Hamilton, M., "A Rating Scale for Depression", *J. Neurol. Neurosurg. Psychiat.*, 23(1): 56 (1960).

Kukolich, L., and Lippman, R., LNKnet User's Guide, MIT Lincoln Laboratory (Feb. 2004).

Lemke, M.P., et al., "Psychomotor Retardation and Anhedonia in Depression", *Acta Psychiatrica Scandinavica* 99(4): 252-256 (1999).

Low, L.-S.A., et al., "Influence of Acoustic Low-Level Descriptors in the Detection of Clinical Depression in Adults", *Proceedings of the 2010 IEEE International Conference on Acoustics, Speech and Signal Processing* (2010).

Moore, II, E., et al., "Critical Analysis of the Impact of Glottal Features in the Classification of Clinical Depression in Speech", *IEEE Transactions on Biomedical Engineering* 55(1): 96-107 (2008).

Moore II, E., et al., "Analysis of Prosodic Variation in Speech for Clinical Depression." *Proceedings of the 25th Annual International Conference of the IEEE EMBS*: 2925-2928 (2003).

Mundt, J.C., et al., "Voice Acoustic Measures of Depression Severity and Treatment Response Collected Via Interactive Voice Response (IVR) Technology", *Journal of Neurolinguistics* 20(1): 50-64 (2007).

Ozdas, A., et al., "Investigation of Vocal Jitter and Glottal Flow Spectrum as Possible Cues for Depression and Near-Term Suicidal Risk", *IEEE Transactions on Biomedical Engineering* 51(9): 1530-1540 (2004).

Ozdas, A., et al., "Analysis of Vocal Tract Characteristics for Near-Term Suicidal Risk Assessment", *Methods Inf Med.* 43(1):36-8 (2004).

Pittam, J. and Scherer, K.R., "Vocal Expression and Communication of Emotion." In *Handbook of Emotions*, Michael Lewis, ed. (NY: Guilford Publications) pp. 185-197 (1993).

Quatieri, T.F., *Discrete-Time Speech Signal Processing: Principles and Practice*, (title page and table of contents) Faye Gemmellaro, ed. (NJ: Prentice Hall PTR) (2001).

Rouas J.-L., "Automatic Prosodic Variations Modeling for Language and Dialect Discrimination," *IEEE Trans. Audio, Speech, and Language Proc.*, 15(6): 1904-1911 (Aug. 2007).

Rouas J.-L., et al., "Rhythmic Unit Extraction and Modeling for Automatic Language Identification," *Speech Communication*,47: 436-456 (2005).

Sapir, S., et al., "Formant Centralization Ratio: A Proposal for a New Acoustic Measure of Dysarthric Speech," *Journal of Speech, Language, and Hearing Research*, 53:114-125 (2010).

Schuller, Björn, et al., "The Interspeech 2009 Emotion Challenge," in Interspeech—2009, pp. 312-315 (2009).

Shen, W., et al., "A Comparison of Query-By-Example Methods for Spoken Term Detection," in Interspeech—2009, pp. 2143-2146 (2009).

Sobin, C. and Sackeim. H.A., "Psychomotor Symptoms of Depression." *American Journal of Psychiatry* 154(1): 4-17 (1997).

Van Heerden, C.J., and Bernard, E., "Speaker-Specific Variability of Phoneme Durations," Paper, (2008).

Van Heerden, C.J., "Phoneme Duration Modelling for Speaker Verification," master's thesis, University of Pretoria (Apr. 2008).

World Health Organization (2001). The World Health Report : 2001 : Mental health : new understanding, new hope. Geneva, World Health Organization.

(56) References Cited

OTHER PUBLICATIONS

James R. Williamson, et al., "Vocal biomarkers of depression based on motor incoordination", Proceedings of the 3$^{rd}$ ACM International Workshop on Audio/Visual Emotion Challenge, AVEC '13, Oct. 21, 2013 (Oct. 21, 2013), pp. 41-48, XP55194796, New York, New York, USA, DOI: 10.1145/2512530.2512531, ISBN 978-1-45-032395-6.

J.R. Williamson, D.W. Bliss; D.W. Browne; J.T. Narayanan, "Seizure prediction using EEG spatiotemporal correlation structure", Epilepsy & Behavior, vol. 25, No. 2, 2012, pp. 230-238, XP002740764, cited in the application the whole document.

Brian S. Helfer, et al., "Classification of depression state based on articulatory precision", Aug. 2013 (Aug. 2013), XP055194854, Retrieved from the Internet: URL:http://citeseerx.ist.psu.edu/viewdoc/download?doi=10.1.1.361.2870&rep=rep1&type=pdf [retrieved on Jun. 10, 2015] the whole document.

Yaozhang Pan et al., "Seizure detection based on spatiotemporal correlation and frequency regularity of scalp EEG", 2012 International Joint Conference on Neural Networks (IJCNN 2012—Brisbane) IEEE Piscataway, NJ, USA, 2012, p. 7 pp., XP002740765, ISBN: 978-1-4673-1488-6 the whole document.

Douglas Sturim et al., "Automatic Detection of Depression in Speech using Gaussian Mixture Modeling with Factor Analysis", 2001, URL:https://wn1.11.mit.edu/mission/cybersec/publications/publication-files/full_papers/2011_06_28_SturimD_Interspeech_FP.pdf.pdf [retrieved on Jun. 10, 2015] the whole document.

\* cited by examiner

USING CORRELATION STRUCTURE OF SPEECH DYNAMICS TO DETECT NEUROLOGICAL CHANGES

RELATED APPLICATION

This application claims the benefit of U.S. Provisional Application No. 61/893,247, filed on Oct. 20, 2013. The entire teachings of the above application are incorporated herein by reference.

GOVERNMENT SUPPORT

This invention was made with Government support under Grant No. FA8721-05-C-0002, Program 2232-41, awarded by the Assistant Secretary of Defense for Research and Engineering (ASD(R&E)). The Government has certain rights in this invention.

BACKGROUND OF THE INVENTION

Major Depressive Disorder (MDD) places a staggering global burden on society. Of all mental disorders, MDD accounts for 4.4% of the total disability-adjusted life years (DALYs) lost and accounts for 11.9% of total years lost due to disability (YLD). With current trends, projection for the year 2020 is that depression will be second only to ischemic heart disease as the cause of DALYs lost worldwide.

A standard method of evaluating levels of MDD in patients includes such questionnaire-based assessment tools such as the 17-question Hamilton Depression Rating Scale (HAMD) and the Beck Depression Inventory (BDI), a 21-question multiple-choice self-report inventory. Both questionnaires result in a score of the patient, which is then translated into a clinical assessment by a physician. Although the HAMD and the BDI assessments are standard evaluation methods, there are well-known concerns about their validity and reliability.

SUMMARY OF THE INVENTION

In one embodiment, the present invention is a method of assessing a condition in a subject. The method comprises the steps of measuring at least one speech-related variable in a subject; extracting a channel-delay correlation structure of the at least one speech-related variable; and generating an assessment of a condition of the subject, based on the correlation structure of the at least one speech-related variable.

In another embodiment, the present invention is a system for assessing a condition in a subject. The system comprises a speech-related variable measuring unit that measures at least one speech-related variable in a subject; a channel-delay correlation structure extractor that extracts a correlation structure of the at least one speech-related variable; and an assessment generator that generates an assessment of a condition in the subject based on the correlation structure of the at least one speech-related variable.

The methods and the systems described herein are advantageously language-independent. Additional advantages include channel-independence as the methods and systems disclosed herein employ data features that do not change with noise or power.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
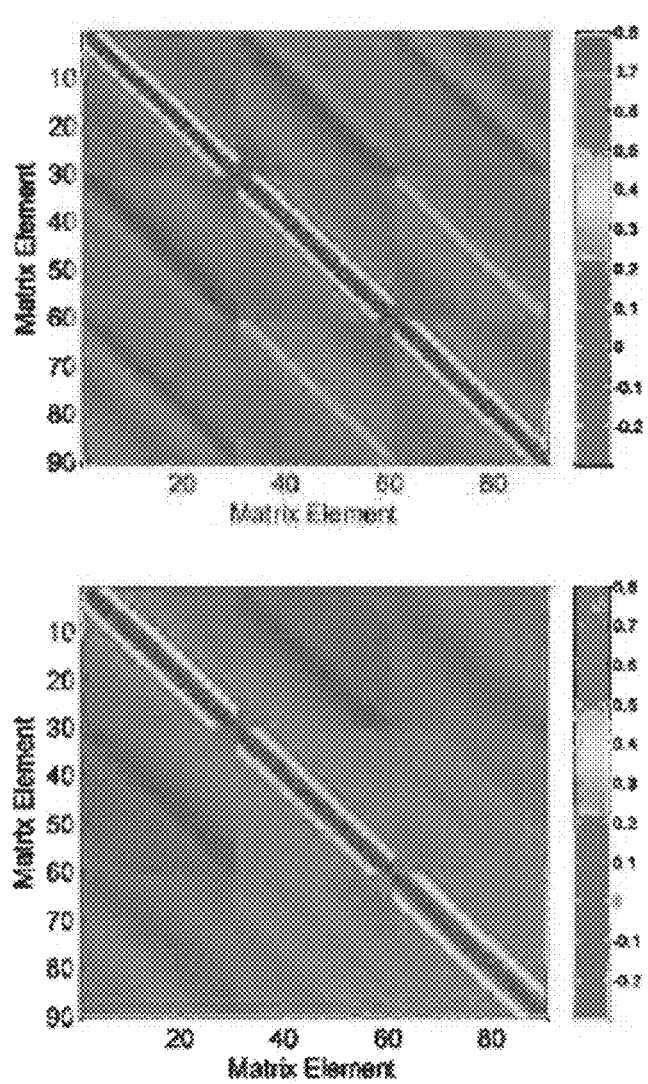
FIG. 1 is a color-coded two-dimensional plot showing an example of a channel-delay correlation matrix computed from formant tracks from a healthy subject (top panel) and from a severely depressed subject (bottom panel).

A description of example embodiments of the invention follows.

As used herein, the term "speech-related variable" means an anatomical or a physiological characteristic of a subject that can be measured during the subject's speech and can serve as a basis for generating an assessment of a condition of the subject, as described herein. Examples of speech-related variables include formant frequencies, as defined below, Mel Frequency Cepstral Coefficents (MFCC) and Delta Mel Frequency Cepstral Coefficents (Delta MFCC), as defined below, prosodic characteristics of speech (that is any characteristic of speech that provides information about the timing, intonation, and/or energy), facial features of the speaker, and skin conductance of the speaker.

Additional examples of speech-related variables include pitch, aspiration, rhythm, tremor, jitter, shimmer, other amplitude- and frequency-modulation functions, as well as their frequency decompositions.

In some embodiments, certain speech-related variables are referred to herein as "low-level features." Such low-level features include the following. Harmonics-to-noise ratio (HNR):HNR is an estimate of the harmonic component divided by the aspiration component in voiced speech, and can act as a measure of "breathiness" in a voice. It is computed over successive frames (e.g., every 10 ms). Aspiration occurs when turbulence is generated at the vibrating vocal folds.

Cepstral Peak Prominence (CPP):

CPP is defined as the difference, in dB, between the magnitude of the highest peak and the noise floor in the power cepstrum for a time interval of greater than about 2 ms and is computed over successive frames (e.g., every 10 ms). (The cepstrum is defined as the Fourier transform of the log-spectrum.) Several studies have reported strong correlations between CPP and overall dysphonia perception, breathiness, and vocal fold kinematics. Facial action units (FAUs). FAU represent measurable differences between facial expressions, and relate to facial features derived from optical video of the face that correspond to muscle movements of the face. The facial action coding system (FACS) quantifies localized changes in facial expression representing facial action units (FAUs) that correspond to distinct muscle movements of the face.

In further embodiments, a speech-related variable is a "pitch slope." The pitch slope is an estimate of the average pitch velocity over each phoneme.

In a certain embodiment, a speech-related variable is not a phone. (As used herein, the term "phone" means "an instance of a phoneme in the actual utterances," where the term "phoneme" means "the smallest structural unit that distinguishes meaning in a language.")

As used herein, a "subject" includes mammals, e.g., humans, companion animals (e.g., dogs, cats, birds, aquarium fish and the like), farm animals (e.g., cows, sheep, pigs, horses, fowl, farm-raised fish and the like) and laboratory animals (e.g., rats, mice, guinea pigs, birds, aquarium fish and the like). In a preferred embodiment of the disclosed methods, the subject is human.

As used herein, a "condition" includes any normal or pathological medical, physiological, emotional, neural, psychological, or physical process or state in a subject that can be identified by the methods disclosed herein. Examples include, but are not limited to stress, traumatic brain injury, dementia, post-traumatic stress disorder, Parkinson's disease, aphasia, autism, Alzheimer's disease, dysphonia, Amyotrophic Lateral Sclerosis (ALS or Lou Gehrig's disease), stroke, sleep disorders, anxiety disorders, multiple sclerosis, cerebral palsy, and major depressive disorder (MDD). In further example embodiments, the condition is selected from traumatic brain injury, post-traumatic stress disorder, Parkinson's disease, aphasia, dysphonia, autism, Alzheimer's disease, Amyotrophic Lateral Sclerosis (ALS), stroke, multiple sclerosis, cerebral palsy, and major depressive disorder (MDD). In a further example embodiment, the condition is selected from traumatic brain injury, dementia, Parkinson's disease, Alzheimer's disease, and major depressive disorder (MDD). Additionally, the term "condition" includes heat/cold exposure effects, effects of sleep deprivation, effects of fatigue and various emotional states such as anger, sadness, or joy.

An "assessment" of the condition can be generated based on any known clinically used scale. Examples of such assessments include quantifiable values by which a condition can be predicted, diagnosed, or monitored by a clinician. Examples of such values include clinical scores, such as Hamilton Depression Rating Scale (HAMD), the Beck Depression Inventory (BDI or Beck score), Quick Inventory of Depressive Symptomatology (QIDS) score, or directly observable physical values such as blood pressure, skin conductance, and pulse rate, among others.

As used herein, the term "channel" refers to a separate source of signal carrying information about the speech-related variable. Each channel can correspond to a unique sensor (such as an EEG electrode) or to a unique extracted component of a signal, such as a feature of a speech signal. Although the speech signal can be detected using a single audio sensor, it can be subsequently separated into multiple channels. Examples of channels include formant frequency, defined below, and to Delta MFCC, defined below.

Figure 7:
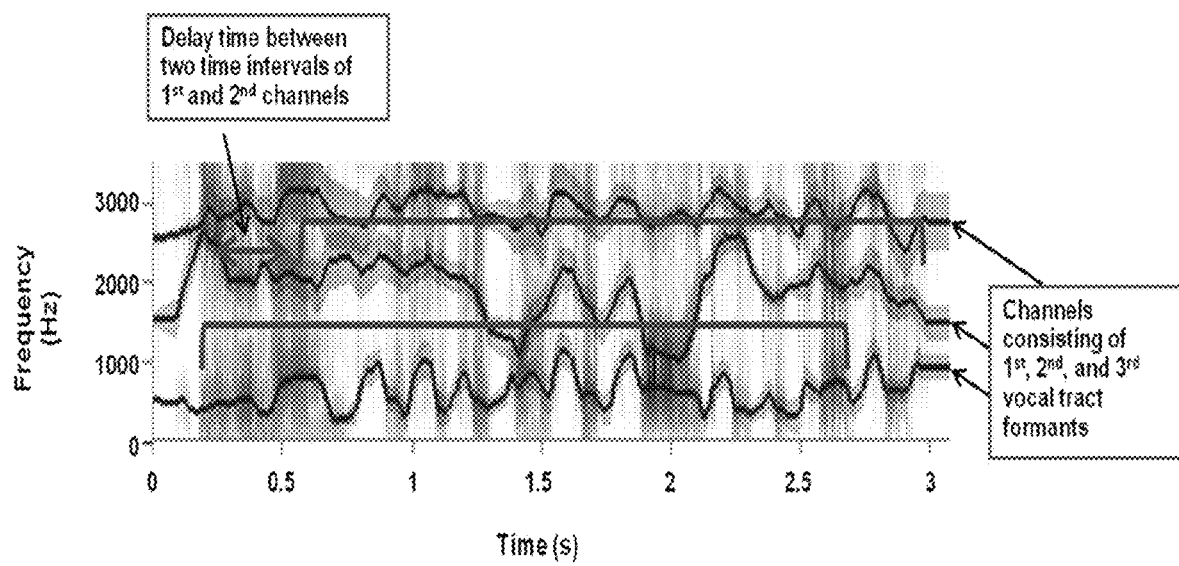
FIG. 7 is an illustration of delay time between two time intervals of two channels where the channels consist of $1^{st}$, $2^{nd}$, and $3^{rd}$ vocal tract formants.

The term "channel-delay," as used herein, refers to a series of values obtained by sampling the signal in a given channel at a certain time point over a certain time interval. The term "delay" refers to the time difference between the starting points of two time intervals. This is illustrated in FIG. 7, which is a plot showing frequency vs. time dependencies of three example vocal tract formants carried over two example channels. Correlation and covariance values can be computed between any two series obtained as described above. For example, auto-correlation can be computed when the series are obtained from the same channel, while cross-correlation can be obtained by using series obtained from different channels.

As used herein, the term "channel-delay correlation structure" refers to a representation of the correlation (both auto- and cross-) or covariance among channel-delay series of values described above. Such a representation can be conveniently expressed as a matrix. In one example embodiment, a channel-delay correlation matrix consists of the correlation coefficients from the Cartesian product of a set of channels and delays.

In various embodiments, the channel-delay correlation structure can employ the correlation or covariance among or between same or different speech-related variables. Sets of speech-related variables employs to compute such channel-delay correlation structure can be referred to as high-level features" or "high-level coordination features." Examples of such high-level coordination features are provided below.

Formant-CPP coordination features: Channel-delay correlation and covariance measures computed between frame-based formant and CPP features.

CPP-coordination features: Channel-delay correlation and covariance measures computed between frame-based HNR and CPP features.

FAU coordination features: Channel-delay correlation and covariance measures computed between pairs of FAUs (time-series at 30 Hz sampling).

Formant-FAU coordination features: Channel-delay correlation and covariance measures computed between frame-based formant and FAU features.

CPP-FAU coordination features: Channel-delay correlation and covariance measures computed between frame-based CPP and FAU features.

HNR-FAU coordination features: Channel-delay correlation and covariance measures computed between frame-based HNR and FAU features.

In another example embodiment, the correlation structure includes the eigenvalues of the channel-delay correlation and covariance matrices, which may be obtained using multiple sets of delays (i.e., multiple delay scales).

In certain example embodiments of the methods described herein, a feature vector consisting of the rank-ordered eigenvalues is constructed from the channel-delay correlation matrix at a given delay scale. From the channel-delay covariance matrix at a given delay scale, in certain example embodiments, it is possible to construct a feature vector containing two elements: (1) the log of the sum of the eigenvalues, and (2) the sum of the log of the eigenvalues.

As used herein, the term "formant frequency" (or "formant") refers to "one of the spectral peaks of the sound spectrum of the voice." A formant frequency usually corresponds to an acoustic resonance of the human vocal tract. It is often measured as an amplitude peak in the frequency spectrum of the sound, often displayed as a spectrogram. Formants are the distinguishing frequency components of human speech. The formant frequencies with the lower values are the "first formants" f1, f2, f3, etc. respectively.

As used herein, the term "Mel Frequency Cepstral Coefficents" (MFCC) refers to the coefficients that collectively make up a "mel-frequency cepstrum" (MFC), which is a representation of the short-term power spectrum of a sound signal. The term "cepstrum" refers to the result of taking the Inverse Fourier transform (IFT) of the logarithm of the spectrum of a signal. The term "mel" refers to the use of the "mel scale" or similar filterbank by the methods that obtain MFCC. The "mel scale" is a perceptual scale of pitches judged by listeners to be equal in distance from one another.

The MFCCs are commonly derived as follows: (1) Take the Fourier transform of a windowed excerpt of a signal. (2) Apply the mel filterbank to the power spectrum obtained in (1), sum the energy in each filter. (The mel-scale filterbank is commonly implemented as triangular overlapping windows.) (3) Take the logarithm of all filterbank energies. (4) Take the discrete cosine transform (DCT) of the list of values obtained in (3) to arrive at the MFCCs. The number of the filters in the mel-scale filter bank dictates the number of MFCCs.

The Delta MFCCs are computed based on the MFCCs as follows:

To calculate the delta coefficients, the following formula can be used:

$$d_t = \frac{\sum_{n=1}^{N} n(c_{t+n} - c_{t-n})}{2\sum_{n=1}^{N} n^2}$$

where $d_t$ is a delta coefficient, from frame t computed in terms of the MFC coefficients ranging from $c_t+N$ to $c_t-N$. A typical value for N is 1 or 2. The number of Delta MFCC is determined by the number of MFCCs.

A person of ordinary skill in the art of speech processing can implement the extraction of formant frequencies and Delta MFCC from a subject's speech using well-known algorithms described, for example in T. F. Quatieri, Discrete-Time Speech Signal Processing: Principles and Practice, Prentice Hall, 2001 (Chapter 5) and D. Mehta, D. Rudoy, and P. Wolfe. Kalman-based autoregressive moving average modeling and inference for formant and antiformant tracking. The Journal of the Acoustical Society of America, 132(3), 1732-1746, 2012. The relevant portions of these publications are incorporated herein by reference.

Accordingly, in an example embodiment, the present invention is a method of assessing a condition in a subject. The method comprises measuring at least one speech-related variable in a subject; extracting a channel-delay correlation structure of the at least one speech-related variable; and generating an assessment of a condition of the subject, based on the correlation structure of the at least one speech-related variable. For example, the speech-related variables can include a formant frequency or, for example, at least two formant frequencies. Alternatively or additionally, the at least one speech-related variable can include a Mel Frequency Cepstral Coefficient (MFCC), or a Delta Mel Frequency Cepstral Coefficient (Delta MFCC) or, for example, at least two Delta MFCCs.

In example embodiments, the channel-delay correlation structure includes channel-delay correlation values and/or channel-delay covariance values. The correlation values and the covariance values can be represented by a channel-delay correlation matrix or a channel-delay covariance matrix, respectively.

In example embodiments, the method of the present invention can be used to generate an assessment of a condition selected from traumatic brain injury, post-traumatic stress disorder, Parkinson's disease, Aphasia, Dysphonia, Autism, Alzheimer's disease, Amyotrophic Lateral Sclerosis (ALS), often referred to as Lou Gehrig's Disease, stroke, sleep disorders, anxiety disorders, multiple sclerosis, cerebral palsy, and major depressive disorder (MDD). In an example embodiment, the condition is MDD.

In an example embodiment, the present invention is a method of assessing MDD in a subject, comprising measuring the first three formant frequencies in a subject; extracting from the first three formant frequencies a correlation structure that includes a channel-delay correlation matrix or a channel-delay covariance matrix; and generating an assessment of MDD in the subject, based on the correlation structure.

In another example embodiment, the present invention is a method of assessing MDD in a subject, comprising measuring the first sixteen Delta MFCCs in a subject; extracting from the first sixteen Delta MFCCs a correlation structure that includes a channel-delay correlation matrix or a channel-delay covariance matrix; and generating an assessment of MDD in the subject, based on the correlation structure.

In an example embodiment, the condition is MDD, and generating the assessment of the condition includes generating an estimate of a Beck score, a Hamilton-D score, or a QIDS score of the subject.

In example embodiments, the method further includes displaying the estimate of the Beck score, the Hamilton-D score, or a QIDS score of the subject.

In an example embodiment, the invention is a system for assessing a condition in a subject. The system comprises a speech-related variable measuring unit that measures at least one speech-related variable in a subject; a channel-delay correlation structure extractor that extracts a correlation structure of the at least one speech-related variable; and an assessment generator that generates an assessment of a condition in the subject based on the correlation structure of the at least one speech-related variable. In example embodiments, the system further includes a display. The display can display the estimate of the Beck score, the Hamilton-D score or a QIDS score of the subject.

The methods and systems disclosed herein can be used as a non-invasive clinical tool, for example for remote assessment of a condition as well as for detection of emotional states of a subject.

The methods and systems of the present invention can employ either an estimation algorithms or a classification algorithm to generate an assessment of a condition. Any known estimation or classification algorithm can be employed.

As used herein, "estimation" is a process of deriving a value (or a measure) related to a condition from a set of speech-related variables. As used herein, "classification" is a process of assigning a condition to one out of a plurality of possible discrete categories based on a set of speech-related variables. Classification for major depressive disorder, for example, might involve categorizing a person as exhibiting clinical depression (category 1) or not exhibiting clinical depression (category 2).

Any of estimation approaches known to a person of ordinary skill in the art can be employed by the example embodiments of the system and methods described herein. Examples include:

weighing the features derived from analyzing the channel-delay correlation structure of a test utterance by a set of values derived from correlations between such features and a condition and summing these weighted values; the weights can optionally be normalized;

employing Pearson correlation and testing for a linear relationship between the features derived from analyzing the channel-delay correlation structure of a test utterance and a measure of a condition;

employing Spearman correlation and testing for a monotonic relationship between the features derived from analyzing the channel-delay correlation structure of a test utterance and a measure of a condition.

Further examples of algorithms suitable for estimation include: minimum mean squared error estimation (MMSE); Bayes least squared error estimation (BLSE); Maximum-likelihood estimation; Maximum a posteriori (MAP) estimation; Bayes estimation; linear classifiers; Fisher's linear discriminant; employing logistic regression; Naive Bayes classifier; Perceptron (a single layer, neural-net classifier which takes features as input and outputs a classification); support vector machines (SVM); least squares support vector machines; quadratic classifiers; kernel estimation; K-nearest neighbor; boosting; decision trees; neural networks; Bayesian networks; and vector quantization.

EXEMPLIFICATION

Example 1: Vocal Biomarkers Based on Motor Incoordination are Indicative of Major Depressive Disorder 1. Introduction In Major Depressive Disorder (MDD), neurophysiologic changes can alter motor control and therefore alter speech production by influencing the characteristics of the vocal source, tract, and prosodies. Clinically, many of these characteristics are associated with psychomotor retardation, where a patient shows sluggishness and motor disorder in vocal articulation, affecting coordination across multiple aspects of production. In this paper, we exploit such effects by selecting features that reflect changes in coordination of vocal tract motion associated with MDD. In a series of experiments, changes in correlation structure that occur at different time scales across formant frequencies and also across channels of the delta-mel-cepstrum were investigated. More specifically, in the series of experiments described below, inter-relationships across aspects of speech production was exploited by selecting features that reflect dynamical changes in coordination within two particular vocal tract representations: (1) formant-frequency tracks, capturing coordination across vocal tract resonant frequencies, and (2) temporal characteristics of mel-cepstral features, capturing coordination in vocal tract spectral shape dynamics. Both feature domains provide measures of coordination in vocal tract articulation while reducing effects of a slowly-varying linear channel, which can be introduced by time-varying microphone placements. With these two complementary feature sets, using the AVEC 2013 depression dataset, a novel Gaussian mixture model (GMM)-based multivariate regression scheme was designed, referred to as Gaussian Staircase Regression. Gaussian Staircase Regression provides a root-mean-squared-error (RMSE) of 7.42 and a mean-absolute-error (MAE) of 5.75 on the standard Beck depression rating scale.

Figure 8A:
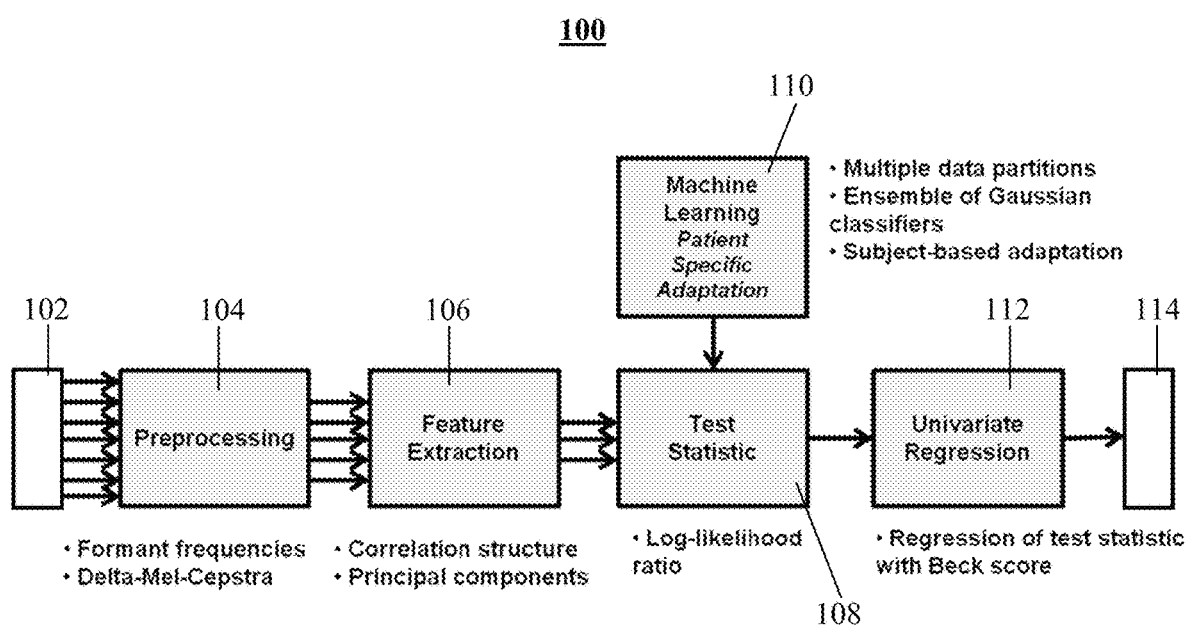
FIG. 8A is a block diagram illustrating an example system and method of the present invention.
Figure 8B:
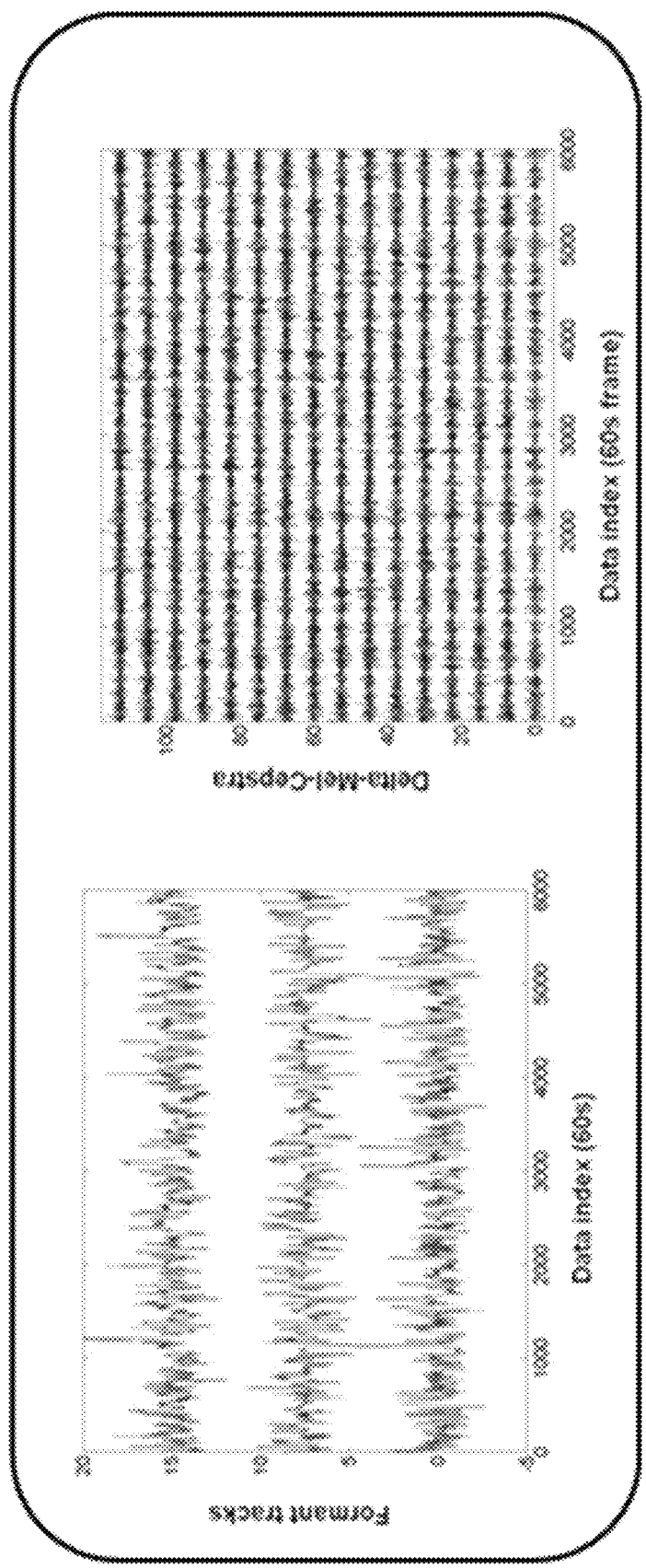
FIG. 8B depicts graphic representation of example formant tracks and Delta-Mel-Cepstral features obtained from the input by the method and system shown in FIG. 8A.

An example embodiment of a system implementing the methods described herein is illustrated in the block diagram shown in FIG. 8A. Method 100 receives input 102 (e.g., subject's speech), which is preprocessed in step 104. The example results of such preprocessing, formant tracks and delta-Mel-Cepstral features, are illustrated in FIG. 8B. The features of input 102 used in the analysis by the method and system described herein are extracted in step 106. The data is statistically analyzed in step 108, using machine learning techniques (step 110). The results of the statistical analysis are subjected to univariate regression in step 112. Method 100 produces output 114, which is, in one embodiment, an assessment of a condition in a subject.

2. AVEC 2013 Database

The AVEC 2013 challenge uses a subset of the audio-visual depressive language corpus (AVDLC), which includes 340 video recordings of 292 subjects performing a human-computer interaction task while being recorded by a webcam and a microphone and wearing a headset. The 16-bit audio was recorded using a laptop sound card at a sampling rate of 41 KHz. The video was recorded using a variety of codecs and frame rates, and was resampled to a uniform 30 frames-per-second. For the challenge, the recording sessions were split into three partitions, with 50 sessions each: a Training, Development, and Test set.

Recording lengths fall between 20-50 minutes with a 25-minute mean value. The mean age is 31.5 years, with a standard deviation of 12.3 years over a range of 18 to 63 years. The recordings took place in a number of quiet environments and consisted of: sustained vowel phonation; speaking loud while solving a task; counting from 1 to 10; read speech; singing; telling a story from the subject's own past; and telling an imagined story. Only the read speech was used (the 3rd read passage).

3. Feature Construction

Two vocal feature domains were selected in which to represent underlying changes in vocal tract shape and dynamics: formant frequencies and delta-mel-cepstra coefficients (Delta MFCC). It was hypothesized that such changes occur with motor control aberrations due to a depressed state. The auto- and cross-correlations among "channels" of each measurement domain become the basis for key depression features.

3.1 Data Segmentation

The goal of data segmentation is to provide, from each session in the Training and Development sets, representative speech data segments with as much extraneous variation removed as possible. It has previously been found that vocal biomarkers for depression assessment are sufficiently reliable when comparing identical read passages. Therefore, it was decided to focus on the third read passage, which has sufficient duration to provide robust feature estimates (mean duration of 226 seconds, with standard deviation of 66 seconds), and which is also in the speakers' common native language (German). This passage was segmented using a semi-automated procedure.

To remove an additional source of extraneous variation, all speech pause segments greater, than 0.75 seconds were detected, and then removed from both of the feature domains, stitching together the feature values across each removed pause segment. This was performed because the presence of long speech pauses provides an extraneous source of low frequency dynamics in the formant and delta-mel-cepstral features that are not necessarily related to depression level. Pause detection was performed using an automated procedure that detects local smooth periods in the formant frequency tracks. These smooth periods occur when the formant tracker (described below) coasts over non-speech or steady regions.

3.2 Formant Frequencies

Vocal tract formant dynamics were loosely associated with vocal articulation as one means to represent articulatory changes in the depressed voice. There are a variety of approaches to the on-going challenge of formant estimation and tracking. We have selected an algorithm recently developed by Rudoy, Mehta, Spendley, and Wolfe based on the principle that formants are correlated with one another in both the frequency and time domains. (See, D. Ruday, D. N. Spcendley, and P. Wolfe. Conditionally linear Gaussian models for estimating vocal tract resonances, Proc. Interspeech. 526-529, 2007 and D. Mehta, D. Rudoy, and P. Wolfe. Kalman-based autoregressive moving average modeling and inference for formant and antiformant tracking. The Journal of the Acoustical Society of America, 132(3), 1732-1746, 2012. The entire teachings of both of these references are incorporated herein by reference.) Formant frequencies are computed at 10-ms data frames. Embedded in the algorithm is a voice-activity detector that allows a Kalman predictor to smoothly coast consistently through nonspeech regions. Because only formant frequencies were used, these features are approximately immune to slowly-varying linear channel effects.

3.3 Mel-Cepstra

To introduce vocal tract spectral magnitude information, standard mel-cepstra (MFCCs) was used, provided by the AVEC challenge, as a basis for a second feature set. Specifically, we use delta-mel-cepstra generated by differencing the first 16 mel-cepstra across consecutive 10-ms data frames, thus introducing a dynamic spectral component and also reducing slowly-varying channel effects through the cepstral difference operation.

3.4 Correlation Structure Features

It was hypothesized that the structure of the correlations of formant frequencies and of delta-mel-cepstral coefficients reflects the physiological coordination of vocal tract trajectories, and thus reveals motor symptoms of depression. A multivariate feature construction approach, based on cross-correlation analysis, was used to characterize the correlation structure among the signals from these two speech feature domains. A detailed description of this feature analysis approach is in J. R. Williamson, D. W. Bliss, D. W. Browne, and J. T. Narayanan. Seizure prediction using EEG spatiotemporal correlation structure. Epilepsy & Behavior, 25(2), 230-238, 2012, incorporated herein by reference in its entirety.

In this approach, channel-delay correlation and covariance matrices were computed from multiple time series channels. Each matrix contained correlation or covariance coefficients between the channels at multiple relative time delays. The approach was motivated by the observation that auto- and cross-correlations of measured signals can reveal hidden parameters in the stochastic-dynamical systems that generate the signals. Changes over time in the eigenvalue spectra of these channel-delay matrices registered the temporal changes in coupling strengths among the channels.

The two feature sets used in this study consisted of the first 3 formants and the first 16 delta-mel-cepstra coefficients, both of which were provided at 10-ms frame intervals. The cross-correlation analysis of these time series was conducted at four different time delay scales. These scales involved computing correlations among time series that were shifted in time relative to each other at four different sample delay spacings: 1, 2, 4, and 8. These spacings corresponded to time delays in increments of 10-ms, 20-ms, 40-ms, and 80-ms.

A multi-scale approach was used to characterize the coupling patterns among the signals over different ranges of delays. For the formant frequency feature set, 30 time delays were used per delay scale, and for the delta-mel-cepstral feature set, 10 time delays were used per delay scale. The formant features were analyzed using a single feature frame that spans the entire data segment, whereas the delta-mel-cepstral features were analyzed using a sliding 60 s feature frame, applied at 30 s intervals.

The results are presented in FIG. 1. FIG. 1 shows channel-delay correlation matrices (3rd delay scale, with time delays in increments of 40-ms) constructed from the formant tracks of two different subjects. These matrices each contain nine 30×30 blocks, each block consisting of the within- or cross-channel correlation coefficients for a pair of formant tracks. These coefficients were computed using all possible pairwise combinations of the 30 time-delayed versions of each channel. The 30×30 blocks along the main diagonal contained the within-channel correlations and the 30×30 off-diagonal blocks contained the cross-channel correlations. The matrix shown in the top panel of FIG. 1 was derived using a healthy subject (Beck score 0) speech. The matrix shown in the bottom panel was derived from a severely depressed subject (Beck score 44) subject's speech. Note that the healthy-subject matrix had a more vivid appearance, containing auto- and cross-correlation patterns that look sharper and more complex.

Figure 2:
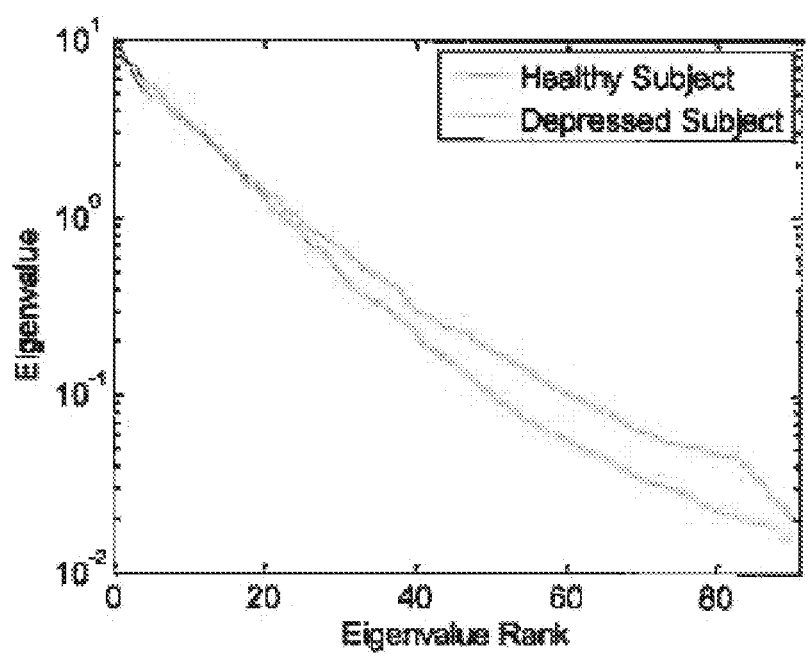
FIG. 2 is a plot of eigenvalues as a function of eigenvalue rank, with eigenvalues ordered from largest to smallest (i.e. an eigenspectra), derived from formant channel-delay matrices shown in FIG. 1.

These qualitative differences between the correlation matrices were quantified using the matrix eigenspectra, which are the rank-ordered eigenvalues. These features were invariant to the underlying ordering of the channels (randomly permuting them will produce identical eigenspectra), capturing instead the levels of correlation among all the channels. The eigenspectra from the two matrices are shown in FIG. 2, with the eigenvalues from the healthy subject in blue and from the depressed subject in red. The eigenspectra from the depressed patient contains a greater fraction of power in the first few eigenvalues, so that there is relatively less high-frequency correlation, indicating reduced complexity and independent variation in this subject's formant tracks. The divergence in eigenspectra between the healthy and the depressed subjects suggested that this technique could provide an effective basis for estimating depression levels.

Additionally, eigenspectra from channel-delay covariance (as opposed to correlation) matrices at each delay scale were also used in order to characterize signal magnitude information. From each covariance eigenspectrum, two summary statistics were computed that capture the overall covariance power and entropy.

The cross-correlation analysis produced, from each feature frame, a high dimensional feature vector of correlation matrix eigenvalues and covariance matrix power and entropy values. These feature vectors consisted of 368 elements in the formant domain (3 formant channels, 4 delay scales, 30 delays per scale, and 2 covariance features per scale), and 648 elements in the delta-mel-cepstral domain (16 delta-mel-cepstral channels, 4 delay scales, 10 delays per scale, and 2 covariance features per scale). The features within each domain were highly correlated, and so the final stage of feature construction was dimensionality reduction, using principal component analysis (PCA), into a smaller set of uncorrelated features. This was done independently within each feature domain. A critical step was to first normalize each of the features into standard units (zero mean unit variance), which allowed the variation of each feature to be considered relative to its baseline variation across the feature frames in all the sessions in the Training set. The top n principal components were input from each domain into the machine learning algorithm for depression estimation, which is described below. The appropriate n was empirically determined independently for each feature domain.

4. GMM-Based Regression Analysis

The feature construction approach described in Section 3.4, above, may produce multiple principal component features that are each weakly correlated with the Beck score. In addition, the patterns of correlation between features and Beck score may differ from one subject to the next. Therefore, a multivariate fusion and regression approach that can effectively combine the information from multiple input features and also take advantage of contextual information such as subject identity (or potentially gender) in making its depression predictions was desired. For this purpose, Gaussian Mixture Models (GMMs) was used in the experiments described herein.

4.1 Multivariate Fusion

The regression approach described herein accomplished fusion of the multivariate feature density for non-depressed (Class 1) and depressed (Class 2) subjects using a novel approach referred to herein as Gaussian Staircase Regression. This approach created a GMM for Class 1 and for Class 2 based on multiple data partitions. The GMMs produced likelihoods for Class 1 and Class 2 on the multiple data frames for each session. The GMM test statistic for a session was the log likelihood ratio of the mean Class 2 likelihoods and mean Class 1 likelihoods. A univariate regression function was then created from the GMM test statistics on the (AVEC) Training set and the corresponding Beck scores. This regression function, when applied to the GMM test statistic from a (AVEC) Development session, was used to produce a Beck score prediction.

Gaussian Staircase Regression used multiple partitions of the Training feature vectors. In each partition, vectors were assigned to the two classes by comparing their Beck scores to a different Beck score threshold. Eight partitions were used, corresponding to Beck score thresholds of 5, 10, . . . , 40. Therefore, rather than the standard approach of training a GMM using Expectation-Maximization from a fixed data partition between depressed and non-depressed subjects, the GMM was formed directly from an ensemble of Gaussian classifiers that were trained from multiple data partitions. This partitioning approach thereby created a "staircase" of increasing Gaussian density support in the feature space for Class 1 along the continuum of lower Beck scores, and for Class 2 along the continuum of higher Beck scores. The Gaussian densities used full covariance matrices, with a constant value of 0.2 added to the diagonal terms for improved regularization.

This approach resulted in a test statistic that tended to smoothly increase with increasing depression, providing a strong basis for subsequent univariate regression. In addition, by using explicit Gaussian densities, it allowed the use of Bayesian adaptation of the Gaussian densities from contextual information such as subject identity (and potentially gender). The Gaussian means were adapted independently in each data partition based on subject identity, using mixing weights computed as $n/(0.5+n)$, where n is the number of 60 s frames from the currently evaluated Development subject that are in the Training set.

The frame rates for correlation structure features were different for the two feature domains, and so multivariate fusion of the principal component features from the two domains required frame registration. The formant-based feature vector is computed using a single frame for each session, whereas the delta-mel-cepstral-based feature vectors are computed using 60 s frames with 30 s overlap. Frame registration was done by duplicating the single formant feature vector from each session, and pairing it (via vector concatenation) with the 6-dimensional delta-mel-cepstral feature vector from each frame, thereby creating the 11-dimensional fused feature vectors. When evaluating the formant features by themselves, these duplicated formant feature vectors were also used, in order to make comparisons over different feature combinations consistent. Using features extracted at fixed time intervals (60 second frames, with 30 second overlap) caused longer duration read passages to produce a larger number of feature vectors, thereby causing these passages to be slightly overrepresented in the Training set.

4.2 Training and Test Procedures

The Beck score predictions were made for each Development session based on parameters estimated from the 50 sessions in the Training set. The Beck score predictions were generated as follows. The high-dimensional correlation structure features from the Training feature frames were normalized to have zero variance and unit standard deviation, and these normalization coefficients were then applied to the high-dimensional correlation structure features from the Development feature frames. Next, PCA was applied independently to each feature domain, generating the following number of components per feature domain: 5 principal components for the formant domain, and 6 principal components for the delta-mel-cepstral domain. As with the feature normalization procedure, the PCA transformation coefficients were determined from the Training features and then applied to the Development features. The principal component features were subsequently normalized to zero mean, unit standard deviation (again, with normalizing coefficients obtained from the Training set only) and applied to the Development set prior to the GMM-based multivariate regression, described in Section 4.1.

The following procedure was repeated for all of the 50 sessions in the Development set to obtain the 50 Beck score predictions. Given the subject identity for each Development session, subject adaptation of the Training set GMMs was performed, and test statistics for the 50 Training set sessions was produced. Because GMM likelihoods were produced at each of multiple feature frames per session, the single test statistic per session was the log likelihood ratio of the mean of the GMM likelihoods for Class 2 and for Class 1. The 50 Training set test statistics were used to create a $2^{nd}$ order regression with the corresponding Training set Beck scores. This regression equation was then applied to the single Development test statistic value to obtain a predicted Beck score for that session. Because negative Beck scores are impossible, negative predictions were set to zero.

5. Prediction Results

Figure 3:
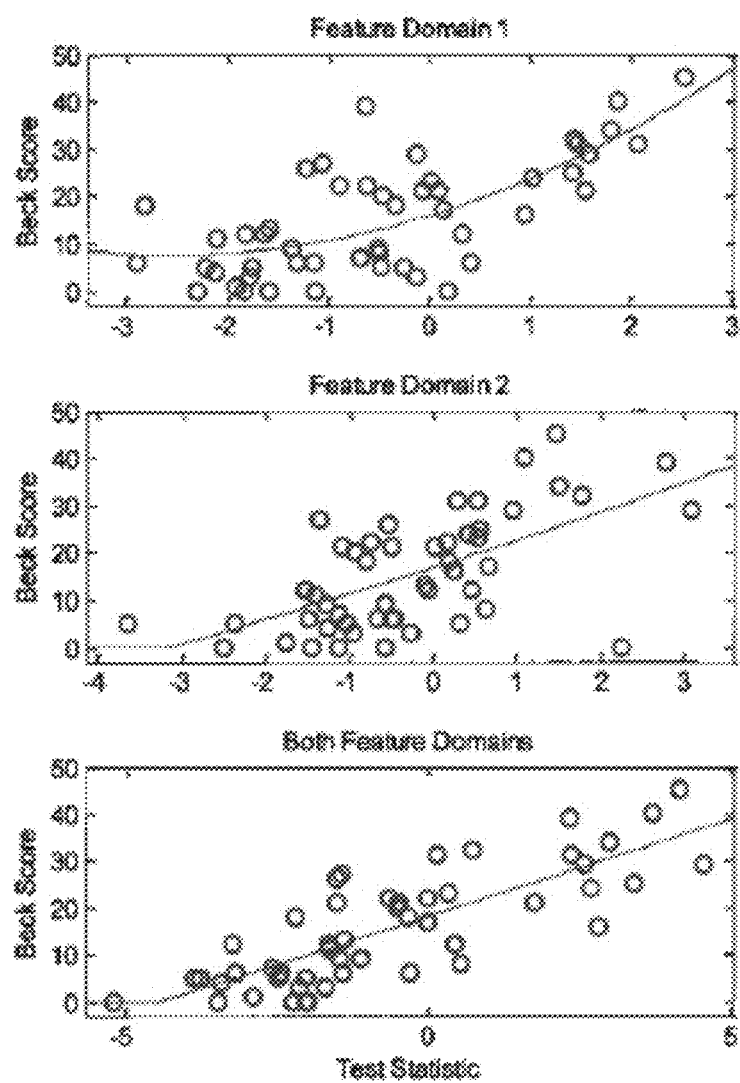
FIG. 3 shows three scatter plots relating GMM test statistics to Beck score on Development set for three feature domain combinations. Top panel is a plot obtained using formant features only. Middle panel is a scatter plot obtained using Delta MFCC features only. Bottom panel is a scatter plot obtained using both feature domains combined.

The feature extraction and regression approach described above was applied to the 3rd read AVEC passage from each session as a basis for predicting depression. FIG. 3 shows scatter plots, with the GMM Development set test statistics on the x-axis and the Development set Beck scores on the y-axis. These plots represent three different combinations of the two feature sets: top panel—formant features only, middle panel—delta-mel-cepstral features only, and bottom panel—both feature domains combined. A solid line shown in each panel represents a $2^{nd}$ order regression fit to these Development test statistics. It is noted that the regressions shown in FIG. 3 are different from those used to generate the Beck predictions. As described in Section 4.2, above, the Beck score predictions were made using different regressions for each Development set subject, based on subject-adapted Training set GMMs.

TABLE 1

Prediction results for three feature domain combinations, with speaker-based adaptation. AVEC baseline audio prediction scores are RMSE = 10.75 and MAE = 8.66 [18].

| Feature Domain | RMSE | MAE | R |
| --- | --- | --- | --- |
| Formant only | 8.50 | 6.87 | 0.68 |
| Delta-mel-cepstral | 9.66 | 7.92 | 0.61 |
| Combined | 7.42 | 5.75 | 0.80 |

Table 1 shows the error metrics and Pearson correlations for the three feature set combinations introduced in FIG. 3. The best Beck score predictions were obtained using the combined feature sets (in which the feature vector consists of 11 principal components), thereby demonstrating their complementary nature. These results had a root-mean-squared-error (RMSE) of 7.42 and a mean-absolute error (MAE) of 5.75 on the standard Beck depression rating scale. These results also demonstrate large performance improvements compared to the AVEC baseline audio prediction scores, which are RMSE of 10.75 and MAE of 8.66.

TABLE 2

Prediction results for three feature domain combinations, without speaker-based adaptation. AVEC baseline audio prediction scores are RMSE = 10.75 and MAE = 8.66 [18].

| Feature Domain | RMSE | MAE | R |
| --- | --- | --- | --- |
| Formant only | 9.97 | 7.92 | 0.56 |
| Delta-mel-cepstral | 10.05 | 8.24 | 0.53 |
| Combined | 8.68 | 7.12 | 0.70 |

Figure 4:
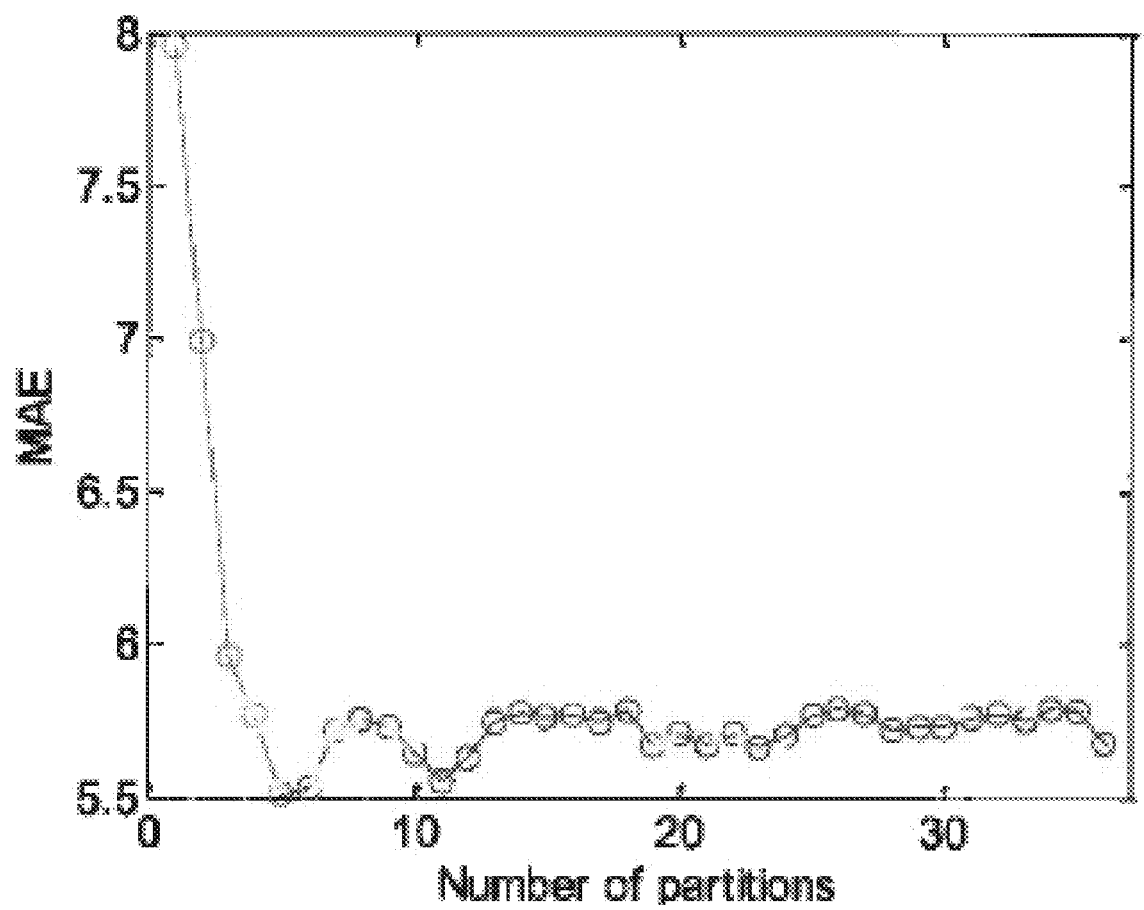
FIG. 4 is a plot of MAE as a function of the number of data partitions used in Gaussian staircase regression.

It is useful to understand the relative importance of different elements of the prediction system. One element is subject-based adaptation of the Gaussian components. Table 2 illustrates the importance of this step, showing that prediction accuracy was degraded if this step was removed. Another element was the use of multiple data partitions in the Gaussian staircase regression technique. The results shown in FIG. 3 and Tables 1 and 2 were obtained with eight data partitions, corresponding to Beck score thresholds of 5, 10, . . . , 40. The effect of varying the number of partitions was also investigated. The results are shown in FIG. 4. The MAE values from the combined features were plotted as a function of the number of data partitions. For multiple partitions, the outside partition threshold values of 5 and 40 were kept fixed, and intermediate threshold values spaced at equal intervals were used. For the single partition case, the midpoint threshold value of 22.5 was used. As FIG. 4 shows, the algorithm was relatively insensitive to the number of partitions, provided there were at least four of them. The number of partitions corresponded to the number of Gaussian components in the Class 1 GMM and Class 2 GMM created by the Gaussian staircase technique. An alternative method of training the GMMs using expectation-maximization from a single fixed data partition was also attempted, but produced inferior results compared to Gaussian staircase regression.

Another interesting data comparison concerned the relative usefulness of mel-cepstral versus delta-mel-cepstral features as input to the cross-correlation analysis technique. Both features were useful, but better performance was established using the delta mel-cepstral features, obtaining MAE=7.92 as opposed to MAE=8.52 for the mel-cepstral features (processed with smallest delay scale only, and three principal components). While using these two cepstral feature sets in conjunction improved performance compared to either one alone (MAE=7.32), it was found that adding the mel-cepstral features to the combined formant and delta-mel-cepstral features slightly degrades performance (MAE=5.92 vs. MAE=5.75).

Figure 5:
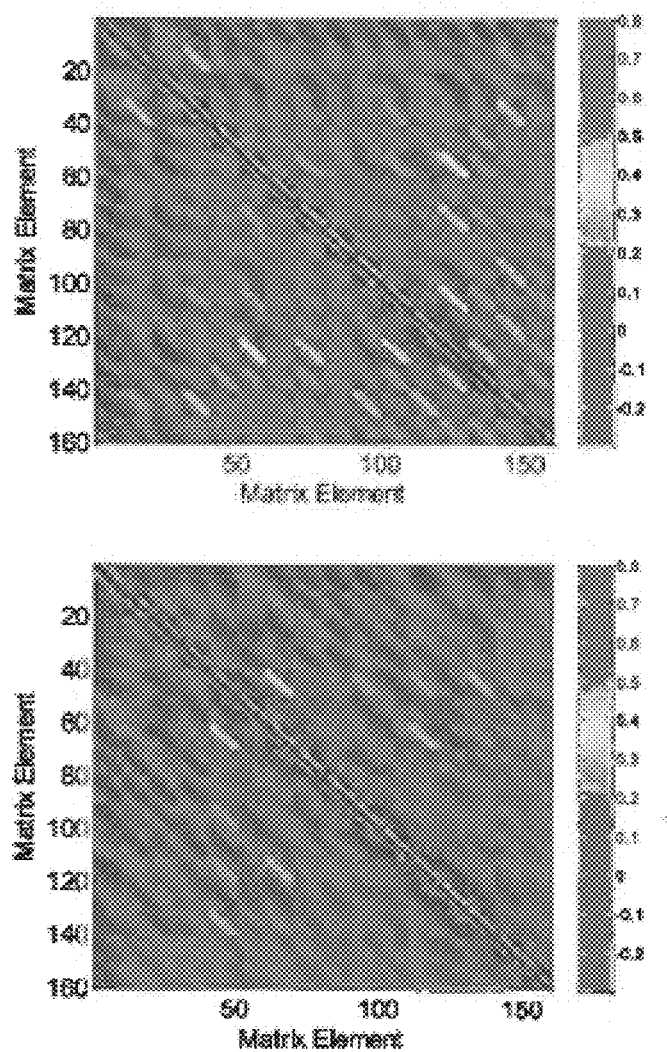
FIG. 5 is a color-coded two-dimensional plot showing examples of channel-delay correlation matrices from delta mel-cepstral features for a healthy subject (top panel) and a depressed subject (bottom panel).
Figure 6:
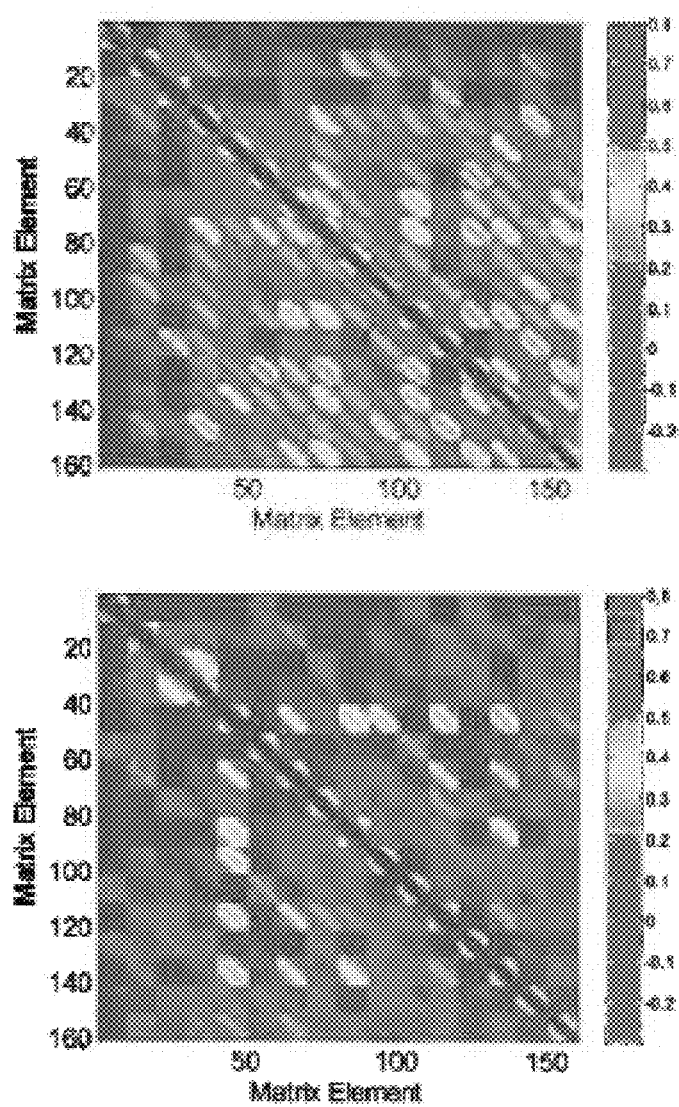
FIG. 6 is a color-coded two-dimensional plot showing examples of channel-delay correlation matrices from mel-cepstral features for a healthy subject (top panel) and a depressed subject (bottom panel).

Insight into these cepstral variants was obtained by viewing examples of their channel-delay correlation matrices. FIG. 5 shows the delta-mel-cepstral matrices at the smallest delay scale for the same healthy and depressed sessions that are also illustrated in FIG. 1 for the formant-based correlation matrices. It was noted that the healthy subject (top panel) showed sharper and less erratic cross-correlation patterns compared to the depressed subject (bottom panel). FIG. 6, on the other hand, shows the corresponding correlation matrices for these sessions derived from the original mel-cepstral features. These matrices showed greater differentiation in the correlations between different channel pairs, which is due to slowly varying channel effects. This resulted in lower relative differentiation within the same channel pair across time delays.

6. Conclusion

The ability to achieve good prediction accuracy of depression using only two vocal feature domains, and only a single, roughly 4-minute long read passage, demonstrates that a solid foundation for depression estimation from vocal biomarkers was achieved.

Example 2: The Use of Additional Speech-Related Variables to Assess Major Depressive Disorder Harmonics-to-Noise Ratio (HNR):

A spectral measure of harmonics-to-noise ratio was performed using a periodic/noise decomposition method that employs a comb filter to extract the harmonic component of a signal. This "pitch-scaled harmonic filter" approach used an analysis window duration equal to an integer number of local periods (four in the current work) and relied on the property that harmonics of the fundamental frequency exist at specific frequency bins of the short-time discrete Fourier transform (DFT). In each window, after obtaining an estimate of the harmonic component, subtraction from the original spectrum yielded the noise component, where interpolation filled in gaps in the residual noise spectrum. The time-domain signals of the harmonic and noise components in each frame were obtained by performing inverse DFTs of the respective spectra. Overlap-add synthesis was then used to merge together all the short-time segments. The short-time harmonics-to-noise ratio is the ratio, in dB, of the power of the decomposed harmonic signal and the power of the decomposed speech noise signal.

Cepstral Peak Prominence (CPP):

There is an interest in developing improved acoustic measures that do not rely on an accurate estimate of fundamental frequency, as required for jitter and shimmer measures A strong correlations between cepstral peak prominence (CPP) and overall dysphonia perception, breathiness, and vocal fold kinematics exists. CPP, defined as the difference, in dB, between the magnitude of the highest peak and the noise floor in the power cepstrum for frequencies greater than 2 ms (corresponding to a range minimally affected by vocal tract-related information) was computed every 10 ms.

Facial Action Unit (FAU):

Measurable differences exist between facial expressions of people suffering from MDD and facial expressions of non-depressed individuals. EMG monitors can register facial expressions that are imperceptible during clinical assessment, and can find acute reductions in involuntary facial expressions in depressed persons. The facial action coding system (FACS) quantifies localized changes in facial expression representing facial action units (FAUs) that correspond to distinct muscle movements of the face. Although the FACS provides a formalized method for identifying changes in facial expression, its implementation for the analysis of large quantities of data has been impeded by the need for trained annotators to mark individual frames of a recorded video session. For this reason, the University of California San Diego has developed a computer expression recognition toolbox (CERT) for the automatic identification of FAUs from individual video frames. Each FAU feature was converted from a support vector machine (SVM) hyperplane distance to a posterior probability using a logistic model trained on a separate database of video recordings. Henceforth, the term FAU refers to these frame-by-frame estimates of FAU posterior probabilities.

In the present study, certain speech-related variables ("high level features") used in this study were designed to characterize properties of coordination and timing of other speech-related variables ("low level features"). The measures of coordination used assessments of the multi-scale structure of correlations among the low-level features. This approach was motivated by the observation that auto- and cross-correlations of measured signals could reveal hidden parameters in the stochastic-dynamical systems that generate the time series. This multivariate feature construction approach—first introduced for analysis of EEG signals for epileptic seizure prediction—has been successfully applied to speech analysis for estimating depression, the estimation of cognitive performance associated with dementia, and the detection of changes in cognitive performance associated with mild traumatic brain injury.

Channel-delay correlation and covariance matrices were computed from multiple time series channels (of given vocal and facial parameters). Each matrix contained correlation or covariance coefficients between the channels at multiple relative time delays. Changes over time in the coupling strengths among the channel signals caused changes in the eigenvalue spectra of the channel-delay matrices. The matrices were computed at four separate time scales, in which successive time delays corresponded to frame spacings of 1, 3, 7, and 15. Overall covariance power (logarithm of the trace) and entropy (logarithm of the determinant) were also extracted from the channel-delay covariance matrices at each scale.

After investigating multiple combinations of the low-level vocal features as input to the xcorr analysis, it was found that the best overall performance is achieved using the following three combinations: 1) Formant-CPP, 2) CPP-HNR, and 3) delta MFCC.

For Formant-CPP xcorr features, vectors consisted of 248 elements (4 channels, 4 time scales, 15 delays per scale, and 2 covariance features per scale). For CPP-HNR xcorr features, vectors consisted of 88 elements (2 channels, 4 scales, 15 delays per scale, top 20 eigenvalues per scale, and 2 covariance features per scale). For delta MFCC xcorr features, the vectors consisted of 968 elements (16 channels, 4 scales, 15 delays per scale, and 2 covariance features per scale).

Facial coordination features were obtained by applying the xcorr technique to the FAU time series using the same parameters that were used to analyze the vocal-based features. Because of the 30 Hz FAU frame rate, spacing for the four time scales corresponded to time sampling in increments of approximately 33 ms, 100 ms, 234 ms, and 500 ms.

EQUIVALENTS

While this invention has been particularly shown and described with references to example embodiments thereof, it will be understood by those skilled in the art that various changes in form and details may be made therein without departing from the scope of the invention encompassed by the appended claims.

What is claimed is:

1. A computer implemented method of assessing a condition of a subject, the method comprising:
    receiving, at a computing device, a digitized microphone signal representing an acoustic signal, including the subject's speech, received at a microphone of the device;
    processing, using the computing device, the digitized microphone signal to produce successive values of at least one speech-related variable;
    determining, using the computing device, a plurality of delays of the at least one speech-related variable;
    calculating, using the computing device, a channel-delay correlation or covariance matrix from the plurality of delays of the at least one speech-related variable;
    determining, using the computing device, a correlation structure of the at least one speech-related variable, including determining a matrix eigenspectrum from the channel-delay correlation or covariance matrix;
    generating, using the computing device, an assessment of the condition of the subject, based at least in part on the matrix eigenspectrum of the correlation or covariance matrix of the correlation structure of the at least one speech-related variable; and
    displaying, on a display, the assessment of the condition of the subject for use by a clinician to predicted, diagnosed, or monitor the condition of the subject.

2. The method of claim 1, wherein the at least one speech-related variable includes a formant frequency.

3. The method of claim 2, wherein the at least one speech-related variable includes two or more formant frequencies.

4. The method of claim 1, wherein the at least one speech-related variable includes a facial action unit, the facial action unit corresponding to muscle movements of the face.

5. The method of claim 1, wherein the at least one speech-related variable includes a Mel Frequency Cepstral Coefficient.

6. The method of claim 1, wherein the at least one speech-related variable includes a Delta Mel Frequency Cepstral Coefficient.

7. The method of claim 6, wherein the speech-related variables are two or more Delta Mel Frequency Cepstral Coefficients.

8. The method of claim 1, wherein the channel-delay correlation or covariance matrix includes channel-delay correlation values.

9. The method of claim 1, wherein the channel-delay correlation or covariance matrix includes channel-delay covariance values.

10. The method of claim 1, wherein the condition is selected from traumatic brain injury, post-traumatic stress disorder, Parkinson's disease, Aphasia, Dysphonia, Autism, Alzheimer's disease, Amyotrophic Lateral Sclerosis, often referred to as Lou Gehrig's Disease, stroke, sleep disorders, anxiety disorders, multiple sclerosis, cerebral palsy, and major depressive disorder.

11. The method of claim 1, wherein the condition is major depressive disorder.

12. The method of claim 1, wherein:
the at least one speech-related variable are includes the first three formant frequencies; and
the condition is major depressive disorder.

13. The method of claim 1, wherein:
the at least one speech-related variable includes the first sixteen Delta Mel Frequency Cepstral Coefficients; and
the condition is major depressive disorder.

14. The method of claim 1, wherein the condition is major depressive disorder, and wherein generating the assessment of the condition includes generating an estimate of a Beck score of the subject, an estimate of a Hamilton-Depression score of the subject, or an estimate of a Quick Inventory of Depressive Symptomatology score of a subject.

15. The method of claim 14, further including displaying the estimate of the Beck score, the Hamilton-Depression score or a Quick Inventory of Depressive Symptomatology score of the subject.

16. The method of claim 1, wherein processing the digitized microphone signal comprises determining a vocal tract representation, and wherein generating the assessment of the condition of the subject is based at least in part on time correlation structure of the vocal tract representation.

* * * * *